United States Patent [19]
Bird

[11] Patent Number: 4,930,501
[45] Date of Patent: * Jun. 5, 1990

[54] VENTILATOR

[76] Inventor: Forrest M. Bird, P.O. Box 817, Sandpoint, Id. 93964

[*] Notice: The portion of the term of this patent subsequent to Jun. 13, 2006 has been disclaimed.

[21] Appl. No.: 237,965

[22] Filed: Aug. 29, 1988

Related U.S. Application Data

[60] Division of Ser. No. 111,139, Oct. 19, 1987, Pat. No. 4,838,260, which is a continuation of Ser. No. 866,790, May 23, 1986, abandoned.

[51] Int. Cl.$^5$ .............................................. A61M 16/00
[52] U.S. Cl. ............................ 128/204.25; 128/205.24
[58] Field of Search ..................... 128/204.18, 204.28, 128/205.24, 205.18, 204.25; 222/207, 209, 301, 304, 265, 897

[56] References Cited

U.S. PATENT DOCUMENTS

| | | | |
|---|---|---|---|
| 2,724,378 | 11/1955 | Wellman | 220/89 A |
| 3,762,595 | 10/1973 | Green et al. | 220/44 R |
| 4,060,078 | 11/1977 | Bird | 128/204.25 |
| 4,127,123 | 11/1978 | Bird | 128/145.8 |
| 4,164,219 | 8/1979 | Bird | 128/204.25 |
| 4,453,197 | 6/1984 | Burrage | 220/89 A |
| 4,592,349 | 6/1986 | Bird | 128/204.25 |

Primary Examiner—Edgar S. Burr
Assistant Examiner—Huong Q. Pham
Attorney, Agent, or Firm—Flehr, Hohbach, Test, Albritton & Herbert

[57] ABSTRACT

Ventilator adapted to be connected to a source of gas comprising a case and an inlet adapted to be connected to the source of gas. It also is comprised of an oscillator cartridge carried by the case having a body with an inlet and an outlet and a flow passage interconnecting the inlet and the outlet. A valve member is carried by the body and is movable between open and closed positions with respect to the outlet. A diaphragm is also carried by the body and is connected to the valve member. A servo port is carried by the body for supplying gas to one side of the diaphragm to cause movement of the diaphragm to move the valve member between open and closed positions to interrupt the flow of gas from the inlet to the outlet. An adjustable impact metering valve is provided for metering the flow of gas to the servo port. A patient adapter and a pneumatic clutching device having an output coupled to the airway of the patient adapter are provided. A one-way check valve couples the adjustable impact metering valve to the outlet from the oscillator cartridge and the pneumatic clutching device. The impact metering valve in combination with said one-way check valve makes it possible to stack successive volumes of gas on the airway of the patient.

4 Claims, 5 Drawing Sheets

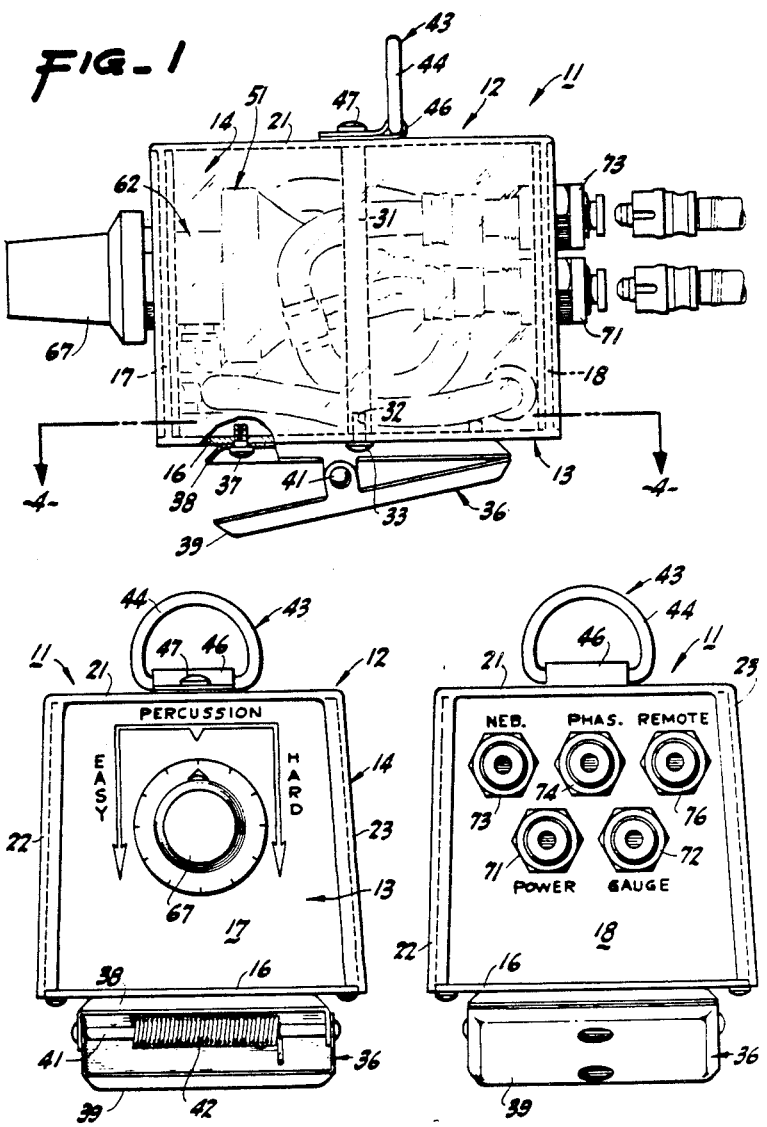

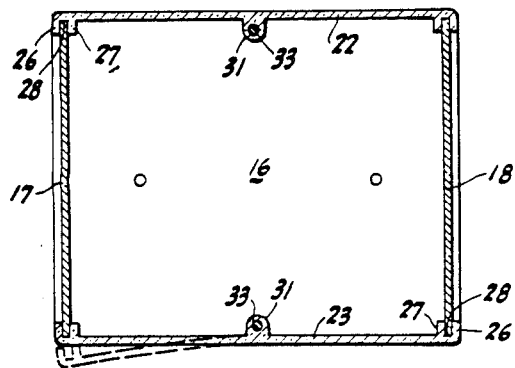
FIG.4
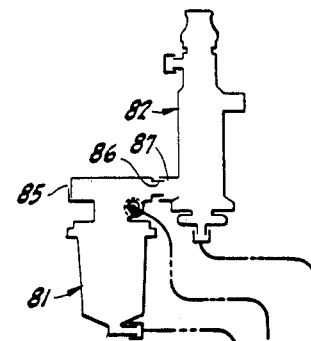
FIG.5
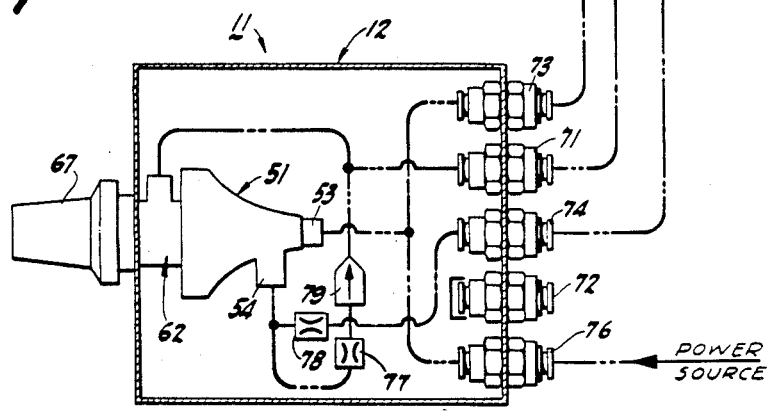

VENTILATOR

This is a division of application Ser. No. 111,139 filed 10-19-87 now Pat. No. 4,838,260 which is a continuation of Ser. No. 866,790, filed 5-23-86, now abandoned.

This application relates to a ventilator and more particularly to a portable-type ventilator.

Ventilators of various types have heretofore been provided such as disclosed in application Ser. No. 671,491, filed on November 14, 1984. The ventilators therein described are relatively complex and do not lend themselves to small compact ventilators which can be readily transported. There is therefore a need for a new and improved ventilator which is very small and compact so that it can be readily transported from one location to another and can be readily carried by the patient so that the patient can be ambulatory.

In general, it is an object of the present invention to provide a ventilator which is small in size and compact.

Another object of the invention is to provide a ventilator of the above character in which the patient is always connected to ambient through a pneumatic clutch.

Another object of the invention is to provide a ventilator of the above character which requires a small amount of gas for its operation.

Another object of the invention is to provide a ventilator of the above character which provides protection against explosive decompression.

Another object of the invention is to provide a ventilator of the above character which has a very small number of parts.

Another object of the invention is to provide a ventilator of the above character which can be inexpensively manufactured.

Another object of the invention is to provide a ventilator of the above character which utilizes a single control knob.

Another object of the invention is to provide a ventilator of the above character in which stacked breaths can be provided.

Additional objects and features of the invention will appear from the following description in which the preferred embodiments are set forth in detail in conjunction with the accompanying drawings.

FIG. 1 is a side elevational view of a ventilator incorporating the present invention.

FIG. 2 is a front elevational view of the ventilator shown in FIG. 1.

FIG. 3 is a rear elevational view of the ventilator shown in FIG. 1.

FIG. 4 is a cross sectional view taken along the line 4—4 of FIG. 1.

FIG. 5 is a physical schematic of the ventilator of the present invention.

Figure 6:
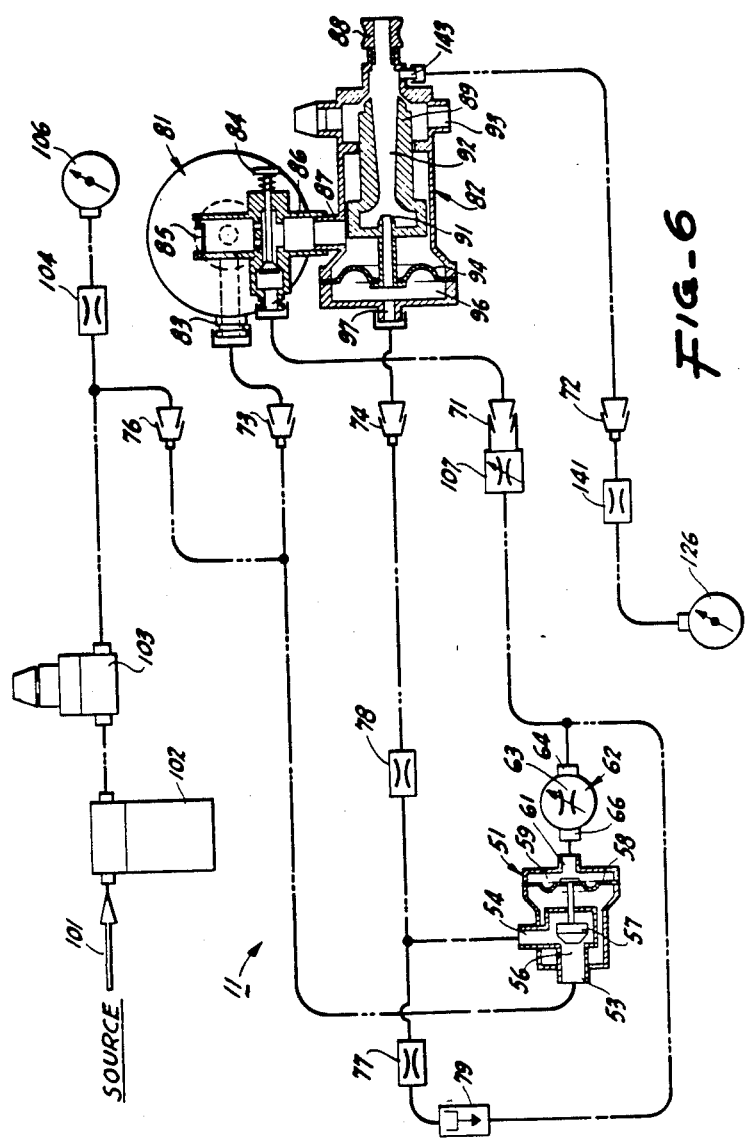
FIG. 6 is a circuit schematic of the ventilator.

In general, the ventilator of the present invention is adapted to be connected to a source of gas. It is comprised of a case having an inlet adapted to be connected to the source of gas. It also consists of an oscillator cartridge carried by the case and having a body, the body having an inlet and an outlet and a flow passage interconnecting the inlet and the outlet, a valve member carried by the body and movable between open and closed positions with respect to the outlet, a diaphragm carried by the body and connected to the valve member, a servo port carried by the body for supplying gas to the diaphragm for causing movement of the diaphragm to thereby cause movement of the valve member between open and closed positions to interrupt the flow of gas from the inlet to the outlet in the body, adjustable metering valve means carried by the case and connected between the outlet of the body and the servo port for metering the flow of gas to the servo port, a patient adapter or interface, pneumatic clutching means having an output connected to the patient adapter and having an input and means coupling the output of the body to the input of the pneumatic clutching means. One way check valve means is provided for coupling the adjustable impact metering valve to the output from the oscillator cartridge. Means is carried by the case to prevent damage to the ventilator in the event of an explosive decompression.

More in particular, the ventilator shown in FIGS. 1, 2, 3, 4 and 5 of the drawings consists of a case 12. The case 12 is formed of two U-shaped parts, 13 and 14. The two U-shaped parts 13 and 14 can be formed with suitable material such as plastic. By way of example, the part 13 can be opaque whereas the part 14 can be formed of a transparent plastic. The U-shaped part 13 is provided with a bottom wall 16 and front and rear walls 17 and 18 which extend at substantially right angles to the bottom wall 16. Similarly, the U-shaped part 14 is provided with a top wall 21 and side walls 22 and 23 which extend at substantially right angles to the top wall 21. Each of the side walls 22 and 23 is provided with a pair of ribs 26 and 27 (see FIG. 4) at each end of the side wall and extending longitudinally of the side wall to provide a slot 28 therebetween. In addition, a rib 31 is formed integral with each of the side walls 22 and 23. The lower extremities of the ribs 31 being provided with holes 32 which receive self-tapping screws 33. The self-tapping screws 33 are utilized to fasten together the two U-shaped parts 13 and 14 with the U-shaped part 14 fitting over the top of the U-shaped part 13 and with the front and rear walls 17 and 18 being received by the slots 28.

A spring clasp 36 of a conventional construction is secured to the bottom wall 16 by suitable means such as self tapping screws 37 secured to one of the members 38 and 39 forming a part of the clasp 36. The members 38 and 39 are hinged by a pivot pin 41. A spring 42 carried by the pivot pin 42 urges the distal extremities of the members 38 and 39 into engagement with each other as shown in FIG. 1. A handle 43 is secured to the top wall 21 of the case 12 and consists of a ring 44 which is carried by a U-shaped clamp 46 secured to the top wall 21 by a self tapping screw 47. The clasp 36 and the handle 43 also can be formed of a suitable material such as metal.

A combination oscillator cartridge and needle valve assembly 51 is carried by the case and is mounted in the front wall 17. It consists of a body 52 having an inlet 53 and an outlet 54 with a flow passage 56 (see FIG. 6) extending between the inlet 53 and the outlet 54. A valve member 57 is carried by the body 52 and is movable between open and closed positions with respect to the outlet for occluding or preventing the flow of gas through the flow passage 56 when the valve member 57 is in the closed position. A diaphragm 58 is also carried by the body 52 and is connected to the valve member for causing movement of the valve member between its open and closed positions. The body 52 provides a chamber 59 on one side of the diaphragm which is in communication with a servo port 61 carried by the body. A needle valve assembly 62 is carried by the body 52 and is provided with an adjustable flow orifice 63 which is connected between the inlet 64 and the outlet 66. The outlet 66 is connected to the servo port 61 of the oscillator cartridge body 52. The needle valve assembly 62 is provided with a knob 67 which is accessible from the front side of the front wall 17 for adjusting the orifice 63.

A plurality of fittings 71, 72, 73, 74 and 76 are mounted on the rear wall 18 as shown particularly in FIG. 3. The fitting 71 can be identified as a power fitting, the fitting 72 as a gauge fitting, the fitting 73 as a nebulizer fitting, fitting 74 as a phasitron fitting and fitting 76 as the remote fitting. A balance orifice 77, a loading orifice 78 and a one-way timing check valve 79 are provided in the case 12 and are interconnected with the combination oscillator cartridge and needle valve assembly 51 and the fittings 71, 72, 73, 74 and 76 by several lengths of tubing as shown schematically in FIG. 5. In addition, certain of the fittings are connected to a nebulizer 81 and a combination venturi and exhalation valve assembly 82 also known as Phasitron. The nebulizer 81 is of a conventional type as described in U.S. application Ser. No. 671,491, filed November 14, 1984. Similarly, the combination venturi and exhalation valve assembly 82 can be of the type described in copending application Ser. No. 516,133 filed July 21, 1983 now U.S. Pat. No. 4,592,349.

The nebulizer 81 is provided with an aerosol power port 83 (see FIG. 6) and a manual push button remote switch 84. It also is provided with a gated inlet 85 for entraining ambient air which is supplied to an outlet 86. The outlet 86 is coupled to an inlet 87 forming a part of the combination venturi and exhalation valve assembly 82. The assembly 82 is provided with an outlet in the form of a patient adapter 88 which is in communication with the inlet 87. The assembly 82 is also provided with a slidable member 89 which carries a jet 91 that introduces gas through a venturi passage 92 provided in the slidable member 89 in communication with the outlet 88. The assembly 82 is provided with an exhaust port 93 which is in communication with the outlet 88. The communication between the exhalation port 93 and the outlet 88 can be interrupted by the slidable member 89 which is movable between open and closed positions with respect to the outlet 88 by a diaphragm 94 which carries the jet 91 and the slidable member 89. A chamber 96 is provided on one side of the diaphragm 96 and is in communication with a servo port 97.

The ventilator 11 is adapted to be operated from a source of gas 101 which is supplied through a filter 102 and from the filter 102 through a pressure reduction regulator 103. As hereinafter described, the gas is supplied to the inlet 53 of the oscillator cartridge body 52. Gas is also supplied through an orifice 104 to an operating pressure gauge 106. A range calibration orifice 107 is provided which is connected to the manual pushbutton 84.

Figure 7:
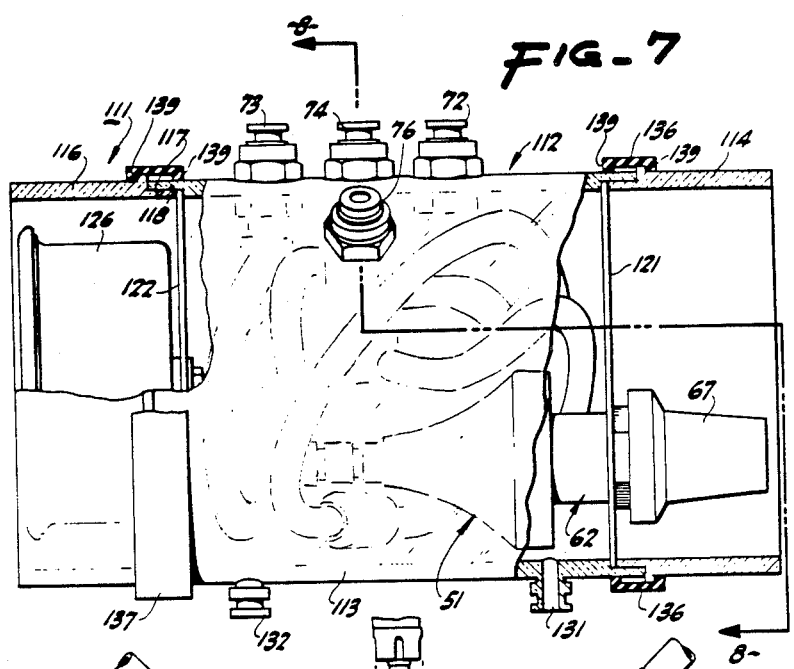
FIG. 7 is a side elevational view of another embodiment of the ventilator incorporating the present invention with certain parts broken away.
Figure 8:
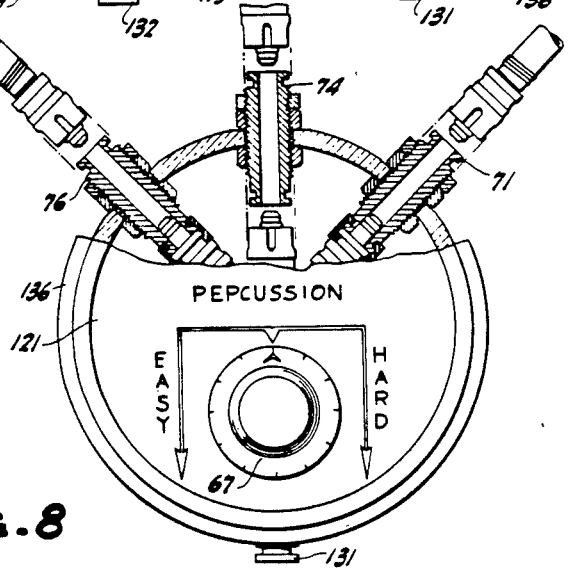
FIG. 8 is a cross sectional view taken along the line 8—8 of FIG. 7.
Figure 9:
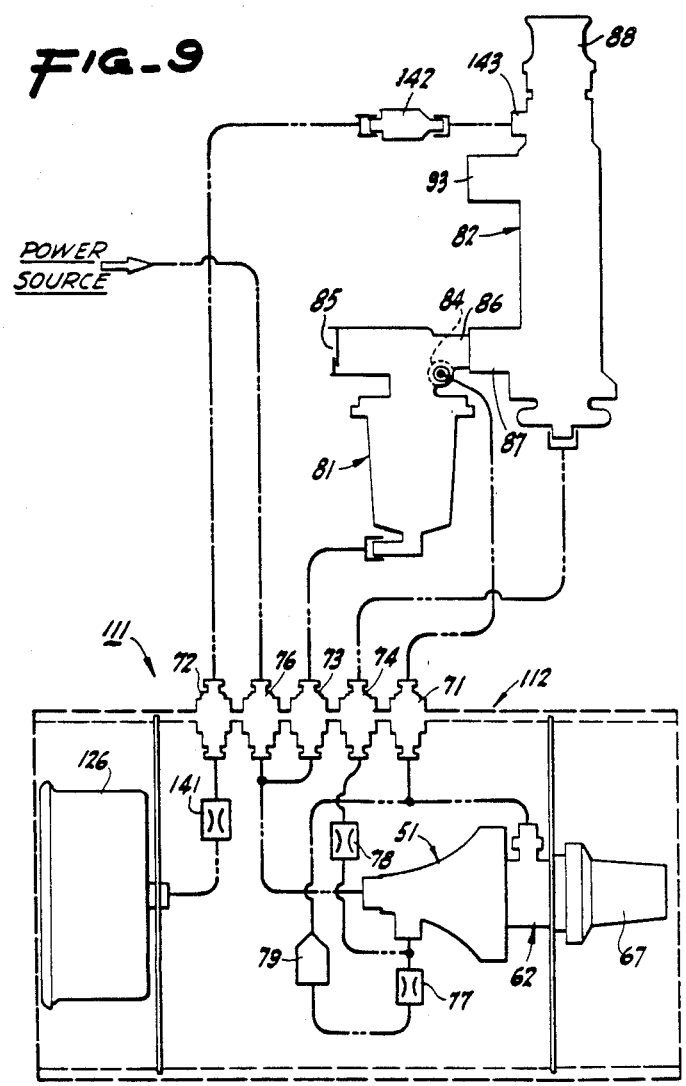
FIG. 9 is a physical schematic of the second embodiment of the ventilator of the present invention.

Operation of this embodiment of the ventilator, ventilator 11 will be described hereinafter in conjunction with another embodiment of the ventilator, ventilator 111 shown in FIGS. 7, 8 and 9. As shown therein, the ventilator 111 consists of a cylindrical case 112. The case 112 consists of a cylindrical central body 113 which has separable end parts 114 and 116 secured thereto on opposite ends thereof. The central body 113 as well as the end parts 114 and 116 can be formed of a suitable material such as a transparent plastic. Cooperative mating means is carried by the ends parts 114 and 116 and the central body 113. This cooperative mating means can take the form of mating internal annular recesses 117 provided on opposite end of the central body 113 and mating external annular recesses 118 provided on one end of each of the end parts 114 and 116. The recesses 117 and 118 are of such a size so that the parts 114 and 116 can be readily mated with the central body 113 to form a friction tight fit.

Circular ends plates 121 and 122 are mounted in the central body 113 and are adapted to seat in the internal annular recesses 117 provided on opposite ends of the central body 113. A combination oscillator cartridge and needle valve assembly 51 of the type hereinbefore described is mounted on the end plate 121 and is provided with a control knob 67 which is accessible from the open end of the end piece 114. A pressure gauge 126 is mounted on the other end plate 122 and is disposed in the end piece 116 so that the face of the pressure gauge 126 is visible from the open end of the end piece 116.

The fittings 71, 72, 73, 74 and 76 provided in the previous embodiment of the ventilator 11 are also provided on the central body 113 with the fittings 72, 73 and 74 being aligned longitudinally of the central body with the fittings 71 and 76 being offset radially with respect to the fittings 72, 73 and 74. A loading orifice 78 and a timing check valve 79 are provided within the case 112.

Explosive decompression means is carried by the case 111 and consists of a pair of fittings 131 and 132 which are mounted in the central body 113 of the case 112 and vent the interior of the case 112 to atmosphere. In addition to the fittings 131 and 132, additional explosive decompression means is carried by the case and takes the form of friction-tight fits which are formed between the end pieces 114 and 116 and the central body 113. In the event of an explosive decompression, the pressure of the gas within the central body 113 between the end plates 121 and 122 will push either one or both of the end plates outwardly against the end parts 114 and 116 sufficient distance so that the end parts are separated from the central body permitting gas to escape around the back sides of the end plate 121 and 122 to atmosphere.

In order to ensure that the end parts 114 and 116 will not accidentally fall off of the central body 113, shock absorbing resilient rings 136 and 137 are provided which slip over the ends of the end parts 114 and 116 and are adapted to overlie the friction joint between the end parts 114 and 116 and the central body 113 to provide additional friction for retaining the end parts 114 and 116 on the central body 113. The rings 136 and 137 are provided with annular raised portions 139 adjacent the side edges of the same which frictionally engage the associated end part and the central body as shown particularly in FIG. 7. These rings 136 and 137 ensure that the end pieces 114 and 116 will not accidentally fall off of the central body and also ensure that significant explosive decompression occurs prior to the end parts 114 and 116 separating from the central body 113.

The gauge 126 is connected through an orifice 141 and a water trap 142 (see FIG. 9) to a pressure monitoring port 143 carried by the combination venturi and exhalation valve assembly 82.

Operation and use of the ventilators 11 and 111 can now be briefly described as follows in conjunction with the pneumatic circuitry shown in FIG. 6. Suitable gas under pressure is supplied to the source 101 through the filter 102 to a pressure reduction regulator 103 to reduce the pressure of the gas to a suitable pressure, for example, 40 to 50 psi. This gas under pressure is supplied through the orifice 104 to operating pressure gauge 106 which gives a reading of the pressure to be supplied to the ventilator. The regulated gas from the regulator 103 is supplied to the power fitting 76 to the inlet 53 of the oscillator cartridge body 52 which is normally open. Gas therefore flows through the outlet 54 and is supplied to a loading orifice 78 of a suitable size such as 0.060 inches through the fitting 74 to supply gas to the inlet 97 of the combination venturi and exhalation valve assembly 82 to supply gas to the jet 91. At the same time gas is supplied to the chamber 97 to apply pressure to one side of the diaphragm 94 so that the slidable venturi body 89 is moved to a closed position to close off exhalation port 93 causing gas to be supplied to the outlet mouthpiece 88 and to the patient. At the same time gas under pressure is supplied through the fitting 76 to the fitting 73 which is connected to the inlet 83 of the nebulizer 81 to cause nebulized gasses to be produced and discharged through the outlet 86 and thence into the inlet 87 of the combination venturi and exhalation valve assembly 82. The nebulized gasses will be entrained by the venturi-like passageway 92 by action of the gasses produced by the jet 91 passing through the venturi-like passageway 92 to thereby cause nebulized gasses to be supplied to the airway and lungs of the patient. The proximal gated inlet port 85 on the nebulizer 81 provides ambient air which can be entrained as needed. The gated inlet port prevents outward flow to ambient during exhalation.

At the time that gasses are supplied to the output 54 of the oscillator cartridge body 52, gasses are supplied through a balance orifice 77, the timing check valve 79 through an impact metering needle valve assembly 62 to the servo port 61 of the oscillator cartridge body 52. The balance orifice 77 serves to provide control over the mean inspiratory rates. Gas is also supplied through the range calibration orifice 107 to the fitting 71 to the manual push button or remote switch 84. However, since this is closed, the only outflow for the gas timing circuit from the impact metering valve 62 is interrupted. The flow of gas into the chamber 59 is controlled by the size of the adjustable orifice 63. As soon as sufficient pressure has been built up in the chamber by the gas entering the chamber, the diaphragm 58 servoes the valve member 57 to a closed position to interrupt the flow of gas from the inlet 53 to the outlet 54. As soon as the oscillator cartridge 52 has been servoed to a closed position, the flow of gas through the combination venturi and exhalation valve assembly is halted. Since the timing check valve 79 only permits one-way flow, the only way gas can escape from the chamber 59 is through the impact metering valve 62 through the range calibration orifice 107 where it leaks down through the manual remote push button switch 84 and out through the combination venturi and exhalation valve assembly 82. The rapidity of which the chamber 59 bleeds down can be controlled by adjusting the range calibration orifice 107. As soon as the chamber has been bled down sufficiently, the oscillator cartridge 52 moves to its normally open position and gas can again flow from the inlet 53 to the output 54 to supply gas to the combination venturi and exhalation valve assembly 82. Gas will again also flow through the timing check valve 79 through the impact metering valve 62 to again begin filling the chamber 59 until sufficient pressure has been provided to move the oscillator cartridge 52 to a closed position to again interrupt the flow between the inlet and the outlet. Thus it can be seen that the oscillator cartridge 52 will oscillate back and forth.

The timing circuit which is provided which includes the impact metering valve 62 in combination with the timing check valve 79 and the range calibration orifice 107 makes it possible to stack breaths on the airway of the patient or successive volumes one on top of the other so as to ensure that there is complete inflation of the lungs of the patient. This makes it possible to bring up the pressure in the lungs and to hold the pressure in the lungs at a predetermined pressure which is just below the clutching pressure for the pneumatic clutching provided by the combination venturi and exhalation valve assembly. Thus, it can be seen that the range calibration valve in conjunction with the adjustable impact metering valve makes it possible to control expiratory time for programmed breath stacking.

The ventilator can be manually cycled by depressing the manual remote push button switch 84 to bleed gas to atmosphere to permit the oscillator cartridge 52 to move to its normally open position to permit the commencement of the inspiratory phase.

From the foregoing it can be seen that the inspiratory and expiratory times are controlled by a single knob 67 provided from the front wall 17 of the ventilator 11. The range calibration orifice 107 determines the ranges.

Good ventilation can be obtained by the patient utilizing the ventilator 11 even though it is relatively simple and compact. The ventilator 11 can be attached to the belt of the patient by the clasp 36 so that the patient can be ambulatory if desired by carrying with him a supply of gas which can be utilized for powering the source 101.

The operation of the ventilator 111 is substantially identical to that hereinbefore described with respect to the operation of the ventilator 11 with the exception that a gauge 126 is provided as a part of the ventilator which measures the proximal airway pressure of the patient.

In the event of explosive decompression, both the ventilators 11 and 111 are provided with means hereinbefore described accommodating such explosive decompression without damaging the ventilator. Thus as shown in FIG. 4, in the event of explosive decompression in the ventilator 11, the pressure within the case 12 can be relieved by one or the other of the side walls 22 or 23 having one side edge of the same be bowed outwardly as shown in broken lines in FIG. 4 to permit the escape of gas in the interior past the outwardly bowed portion. As soon as the pressure has been released, the bowed out portion will spring back automatically into its normal position and in engagement with the front wall 17. It should be appreciated that although only one portion of a wall is shown being bowed out by explosive decompression, one or more additional portions of the side walls 22 and 23 can be bowed out in a similar manner to relieve the pressure of the gas within the case to the atmosphere. This ensures that the gas will be exhausted without any damage to the ventilator.

As explained previously, explosive decompression means is also associated with the ventilator 111. In the case of an explosive decompression, the initial gasses will be vented through the fittings 131 and 132. If this is insufficient to permit a rapid escape of the gasses during an explosive decompression, the gasses can force the end plates 121 and 122 outwardly against the frictional engagement of the end pieces 114 and 116 with the center section 113 for a sufficient distance so that air within the central body 112 can escape to the atmosphere. The resilient rings 136 and 137 will permit the interior gasses to be vented to the atmosphere without endangering the ventilator. In the event there is some displacement of the end pieces 114 and 116 because of an explosive decompression, they can be readily reestablished in their proper positions merely by fitting the end pieces on to the central body and thereafter placing the resilient rings 136 and 137 over the mating parts of the same.

It is apparent from the foregoing that there has been provided a ventilator which is relatively small and compact. It is constructed in such a manner so that it can be economically manufactured. The ventilators are provided with a simple single control which makes it possible to change both the inspiratory and expiratory phases. The case is also constructed in such a manner so that it can be readily assembled and disassembled.

What is claimed is:

1. In small compact light weight ventilator adapted to be connected to a source of gas and adapted to be carried on the person of a patient so that gas can be supplied to the airway of the patient, a case having a cylindrical configuration, an inlet mounted on the case adapted to be connected to the source of gas, an oscillator cartridge mounted in the case and having a body, the body having an inlet and an outlet and a flow passage interconnecting the inlet and the outlet, diaphragm means mounted within the body, a valve member disposed on one side of the diaphragm means and connected to the diaphragm means and being movable between open and closed positions with respect to the outlet, a servo port on the other side of the diaphragm means for supplying gas to the other side of the diaphragm to cause movement of the diaphragm means to thereby move the valve member between open and closed positions to interrupt the flow of gas from the inlet to the outlet, means connecting the inlet of the oscillator cartridge to the inlet mounted on the case, an adjustable impact metering valve having an inlet and an outlet, a patient adapter adapted to be coupled to the airway of the patient, pneumatic clutching means having an output coupled to the patient adapter, one-way check valve means coupling the inlet of the adjustable impact metering valve to the outlet of the oscillator cartridge, means coupling the outlet of the impact metering valve to the servo port, range calibration means connected to the inlet of the impact metering valve and, via said one-way check valve means, to the outlet of the oscillator cartridge and manually operated valve means connecting the range calibration means to the pneumatic clutching means, said adjustable impact metering valve providing a single control for the ventilator and in combination with said one-way check valve means and said range calibration means making it possible to stack successive volumes of gas on the airway of the patient, said manually operated valve being movable between open and closed positions and in an open position coupling the servo port to the pneumatic clutching means to interrupt the stacking of the successive volumes of gas.

2. A ventilator as in claim 1 together with explosive decompression means carried by the case.

3. In a ventilator adapted to be connected to a source of gas to supply gas to the airway of a patient, a case, an inlet adapted to be connected to the source of gas, an oscillator cartridge mounted in the case and having a body, the body having an inlet and an outlet and a flow passage interconnecting the inlet and the outlet, a valve member carried by the body and movable between open and closed positions with respect to the outlet, diaphragm means mounted within the body and connected to the valve member, a servo port carried by the body for supplying gas to one side of the diaphragm means to cause movement of the diaphragm means to thereby move the valve member between open and closed positions to interrupt the flow of gas from the inlet to the outlet, an adjustable impact metering valve having an inlet and an outlet for metering the flow of gas to the servo port, a patient adapter, pneumatic clutching means having an output coupled to the airway of the patient adapter, one-way check valve means coupling the adjustable impact metering valve to the outlet of the oscillator cartridge means coupling the outlet of the impact metering valve to the servo port, range calibration means connected to the inlet of the impact metering valve and, via said one-way check valve means to the outlet of the oscillator cartridge, manually operated valve means connecting the range calibration means to the pneumatic clutching means, said impact metering valve in combination with said one-way check valve means making it possible to stack successive volumes of gas on the airway of the patient, said manually operated valve being movable between open and closed positions and in an open position coupling the servo port to the pneumatic clutching means to interrupt the stacking of successive volumes of gas, said case being formed of a central portion, first and second cylindrical end portions and cooperative mating means carried by the end pieces and the central body permitting frictional engagement of the end pieces with the extremities of the body, end plates carried by the central body and disposed between the end pieces and the central body whereby in the event of an explosive decompression, the end pieces are urged outwardly against the frictional force bonding the end pieces to the central body to permit gas to escape between the end pieces and the central body to accommodate explosive decompression without damage to the case.

4. A ventilator as in claim 3 together with resilient shock absorbing rings carried by the case and overlying the cooperative mating means and the central body.

* * * * *